(12) United States Patent
Melodelima et al.

(10) Patent No.: US 10,327,732 B2
(45) Date of Patent: Jun. 25, 2019

(54) METHOD FOR CHARACTERISING AN ULTRASOUND WOUND IN ORGANIC TISSUES

(71) Applicants: EDAP TMS FRANCE, Vaulx-en-velin (FR); INSERM (INSTITUT NATIONAL DE LA SANTE ET DE LA RECHERCHE MEDICALE), Paris (FR)

(72) Inventors: David Melodelima, Ruy (FR); Jeremy Vincenot, Les Haies (FR); Emmanuel Blanc, Saint Didier Au Mont D'or (FR)

(73) Assignees: EDAP TMS FRANCE, Vaulx-en-Velin (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 520 days.

(21) Appl. No.: 14/917,605

(22) PCT Filed: Oct. 7, 2014

(86) PCT No.: PCT/FR2014/052539
§ 371 (c)(1),
(2) Date: Mar. 9, 2016

(87) PCT Pub. No.: WO2015/052428
PCT Pub. Date: Apr. 16, 2015

(65) Prior Publication Data
US 2016/0220224 A1    Aug. 4, 2016

(30) Foreign Application Priority Data
Oct. 8, 2013    (FR) ...................... 13 59727

(51) Int. Cl.
*A61B 8/08*    (2006.01)
*G06T 7/00*    (2017.01)
(Continued)

(52) U.S. Cl.
CPC ............... *A61B 8/085* (2013.01); *A61B 8/08* (2013.01); *A61B 8/0833* (2013.01); *A61B 8/14* (2013.01);
(Continued)

(58) Field of Classification Search
CPC .. A61B 5/055; A61B 6/50; A61B 8/08; A61B 8/085; A61B 8/14; A61B 8/5223;
(Continued)

(56) References Cited

U.S. PATENT DOCUMENTS 5,738,635 A * 4/1998 Chapelon ................. A61F 7/00
601/2
2005/0240126 A1* 10/2005 Foley ....................... A61B 8/06
601/2
(Continued)

OTHER PUBLICATIONS

Righetti et al. "Elastographic Characterization of HIFU-Induced Lesions in Canine Livers." Ultrasound in Medicine & Biology 25(7), pp. 1099-1113. (Year: 1999).*
(Continued)

*Primary Examiner* — Amanda Lauritzen Moher
(74) *Attorney, Agent, or Firm* — Ladas & Parry LLP; Malcolm J. MacDonald

(57) ABSTRACT

The method of characterizing an ultrasound lesion (T) in organic tissues, the lesion being made by applying high intensity focused ultrasound delivered by a probe having its emission surface presenting a shape that is toroidal, consists in: after a period of at least two days from the end of ultrasound application, acquiring at least one characterization image (Ic) of the organic tissues; detecting the presence
(Continued)

of a contrast border (16) in the characterization image (Ic); and from the contrast border (16), determining the extent of the ultrasound lesion.

22 Claims, 2 Drawing Sheets

(51) Int. Cl.

| | |
|---|---|
| G06T 7/10 | (2017.01) |
| G06T 7/13 | (2017.01) |
| G06T 7/11 | (2017.01) |
| G06T 7/12 | (2017.01) |
| G06T 7/60 | (2017.01) |
| A61N 7/00 | (2006.01) |
| A61N 7/02 | (2006.01) |
| A61B 8/14 | (2006.01) |
| G06T 7/174 | (2017.01) |
| A61B 5/00 | (2006.01) |
| A61B 17/32 | (2006.01) |
| A61B 6/00 | (2006.01) |
| A61B 5/055 | (2006.01) |

(52) U.S. Cl.
CPC .............. *A61B 8/5223* (2013.01); *A61N 7/00* (2013.01); *A61N 7/02* (2013.01); *G06T 7/001* (2013.01); *G06T 7/0012* (2013.01); *G06T 7/10* (2017.01); *G06T 7/11* (2017.01); *G06T 7/12* (2017.01); *G06T 7/13* (2017.01); *G06T 7/60* (2013.01); *A61B 5/055* (2013.01); *A61B 5/4312* (2013.01); *A61B 6/50* (2013.01); *A61B 8/0825* (2013.01); *A61B 17/320068* (2013.01); *G06T 7/174* (2017.01)

(58) Field of Classification Search
CPC ...... A61B 8/0833; A61N 7/02; G06T 7/0012; G06T 7/60; G06T 7/12; G06T 7/11; G06T 7/13; G06T 7/10; G06T 7/001; G06T 7/174
See application file for complete search history.

(56) References Cited

U.S. PATENT DOCUMENTS

2007/0073254 A1 3/2007 Ponomarenko et al.
2008/0033323 A1 2/2008 Meirer et al.

OTHER PUBLICATIONS

Nishida. Precipitation of Calcium Carbonate by Ultrasonic Irradiation. Ultrasonics Sonochemistry 11: 423-428. (Year: 2004).*
Gary Y Hou et al:"Performance Assessment of HIFU Lesion Detection by Harmonic Motion Imaging for Focused Ultrasound (HMIFU): A 3-D Finite-Element-Based Framework with Experimental Validation", Ultrasound in Medicine and Biology, New York, NY, US, vol. 37, No. 12, Sep. 6, 2011, pp. 2013-2027.
Sheng Yan et al.:"Ultrasound image enhancement for HIFU lesion detection and measurement", 9th International Conference on Electronic Measurement & Instruments, 2009:ICEMI'09; Aug. 16-19, 2009, Beijing, China; Proceedings, IEEE, Piscataway, NJ, USA, Aug. 16, 2009, pp. 4-193-4-194.
Noble J A et al.:"Ultrasond image segmentation: a survey", IEEE Transactions on Medical Imaging, IEEE Service Center, Piscataway, NJ, US, vol. 25, No. 8, Aug. 1, 2006, pp. 987-1010.

* cited by examiner

METHOD FOR CHARACTERISING AN ULTRASOUND WOUND IN ORGANIC TISSUES

This application is a 371 of PCT/FR2014/052539, filed on Oct. 7, 2014, which claims priority to French Application No. 1359727, filed Oct. 8, 2013.

The present invention relates to the technical field of high intensity focused ultrasound (HIFU) and it relates more precisely to characterizing a lesion in organic tissues caused by applying focused ultrasound waves.

In the treatment of localized solid cancerous tumors, the best therapeutic option usually remains surgical excision. That enables the cancerous tissue to be removed and, providing the surgical margins are negative, it also minimizes the risk of localized metastases.

Nevertheless, that therapeutic approach presents two constraints:
surgery is invasive and can reduce the benefit/risk ratio of the treatment;
it is necessary to ensure that the surgical margins are negative, i.e. that all of the tumor cells have indeed been removed.

HIFU therapeutic technology provides an advantageous solution that is minimally invasive. The principle consists in focusing an ultrasound beam on the tumor zone for destruction that is also referred to as the "target" zone. The absorption of ultrasound energy by biological tissues leads to a large increase in temperature that causes immediate and irreversible necrosis of the tissue at the focal point of the ultrasound beam while sparing tissues situated intermediately between the ultrasound transducer and the focal point.

In contrast, since the treatment is not invasive, the problem of monitoring the treatment margins is complex. During excision, the surgeon can take samples of biological tissues, analyze them, and verify the surgical margins in order to decide whether or not to extend the intervention (extemporaneous analysis). This sample taking and analysis cannot be done when performing non-invasive HIFU treatment.

Several solutions can be envisaged for addressing this problem. They all rely on preoperative or postoperative imaging of high quality that makes it possible to visualize accurately the location of the tissue zone for destruction. At this stage, therapy margins are often established, i.e. some minimum distance around the target zone over which the treatment is to be extended. During the treatment, real-time imaging devices make it possible to image the organ being treated, to view the target zone, and to position the therapeutic device relative thereto. At the end of the treatment, several solutions can then be proposed for monitoring the therapeutic margins depending on whether or not the biological lesion that has been made is visible with the imaging means associated with the treatment device.

When the biological lesion is not visible (radiotherapy treatment, focused ultrasound treatment on certain organs such as the prostate), computer tools (multimode image merging) are often used for confirming that the therapeutic device was properly positioned in compliance with preoperative planning. Nevertheless, in spite of using such "retouching" tools, it is appropriate to use therapeutic margins that are wide enough to be certain that all of the target zone has been treated.

When the biological lesion that has been made is visible, it is possible to observe margins visually and the operator can verify in various section planes that the biological lesion does indeed cover all of the target zone. Nevertheless, it is still appropriate to verify that the biological lesion, as visualized, is indeed representative of the biological tissue zone that has been destroyed. By way of example, the image of the destroyed biological zone may rely on local devascularization of the tissue caused by the therapeutic principle giving rise to a low-level signal in magnetic resonance imaging (MRI) or in ultrasound imaging. Nevertheless, devascularization is not absolutely representative of cell death and a risk of local metastases cannot be totally set aside.

Without having imaging means that are accurately representative of cell death and compatible with non-invasive examination, the problem of inspecting therapeutic margins during minimally invasive treatment remains incompletely solved.

New ultrasound imaging techniques, also referred to as echographic imaging, are being developed in order to attempt to image tissue lesions that are not observable with conventional echographic imaging of B-mode type (two-dimensional brightness mode).

Some rely on the difference in elasticity of tissue after it has been heated by ultrasound treatment (elastographic imaging). The document: "*Performance assessment of HIFU lesion detection by harmonic motion imaging for focused ultrasound (HMIFU): a 3-D finite element-based framework with experimental validation*", by Gary Y. Hou et al., *Ultrasounds in Medicine and Biology*, New York, N.Y., US, Vol. 37, No. 12, Sep. 6, 2011, describes such a method. Those methods are complex and require imaging systems that are specific and expensive, and that are not universally deployed.

Specific image processing algorithms nevertheless make it possible to enhance the differences in contrast between treated and non-treated tissues in a conventional echographic image of B-mode type. Such methods are complex and often lack sufficient robustness for practical clinical application. The document: "*Ultrasound image enhancement for HIFU lesion detection and measurement*" by Sheng Yan et al., 9th International Conference on Electronic Measurement & Instruments, 2009-Aug. 16-19, 2009, Beijing, China—Proceedings, IEEE, pp. 4-193-ISBN: 978-1-4244-3863-1-Section III Experimental result on HIFU monitor image, proposes such a method. Although enhancing contrast differences makes it easier to distinguish between treated and non-treated tissues, which is referred to as segmentation, it is still necessary to have recourse to powerful algorithms in order to enable outlines of the treated zone to be segmented automatically. The document: "*Ultrasound segmentation: A survey*", by J. Alison Noble, *IEEE Transactions on Medical Imaging*, Vol. 25, No. 8, August 2006, pp. 987-1010, proposes a review of recent developments in the field of segmentation and emphasizes the particular difficulty of this problem in the field of ultrasound imaging.

The above-mentioned methods of image processing and segmentation remain complex and are still not sufficiently robust to be used on a generalized basis. There thus appears a need to develop a method of characterizing lesions in organic tissues treated with methods that are non-invasive or minimally invasive, such as HIFU treatments.

The invention thus provides a method of characterizing an ultrasound lesion in organic tissues, the lesion being made by applying high intensity focused ultrasound delivered by a probe having its emission surface presenting a shape that is toroidal or pseudo-cylindrical.

According to the invention, the method consists in:
  after a period of at least two days from the end of ultrasound application, acquiring at least one characterization image of the treated organic tissues;
  detecting the presence of a contrast border in the image; and
  from the contrast border, determining the extent of the ultrasound lesion.

In particular implementations, the method presents one or more of the following additional characteristics, or indeed all of them:
  detecting, in the characterization image, the presence of a contrast border that is closed;
  identifying, in the characterization image, the ultrasound lesion inside the contrast border;
  acquiring an ultrasound characterization image, and identifying, within the contrast border of the ultrasound characterization image, a high-level echo zone and a low-level echo zone located close to the high-level echo zone and the contrast border;
  acquiring a reference image of the organic tissues prior to applying the ultrasound, so as to visualize the tumor and compare the reference image with the characterization image in order to monitor therapeutic margins;
  processing the reference and characterization images in order to determine the extent of the ultrasound lesion;
  calculating a ratio between the area defined by the ultrasound lesion in the characterization image and the area defined by the tumor in the reference image in order to deduce a margin size for the extent of the lesion;
  using a plurality of characterization images and a plurality of reference images to calculate a ratio between the volume defined by the ultrasound lesion in the characterization images and the volume defined by the tumor in the reference images in order to deduce therefrom a margin size for the extent of the ultrasound lesion;
  acquiring the characterization image after a period lying in the range six days to thirty days, and preferably of about eight days; and
  characterizing the lesion of organic tissues corresponding to liver tissues.

The above-defined characterization method does not contain a step seeking to apply high intensity focused ultrasound, and thus it excludes any step of surgical or therapeutic treatment of the human or animal body. It seeks only to characterize a lesion that is supposed to have been caused by such treatment. It may comprise one or more steps that are performed before such treatment, but nevertheless it does not include the treatment.

Furthermore, the invention also provides a method of treating and characterizing biological tissues in a human or animal body, the method comprising a treatment step including a step of applying high intensity focused ultrasound as delivered by a probe having its emission surface presenting a shape that is toroidal or pseudo-cylindrical, to biological tissues within a human or animal body, and including the characterization method as defined above.

Various other characteristics appear from the following description made with reference to the accompanying drawings, which show implementations of the invention as non-limiting examples.

Figure 1:
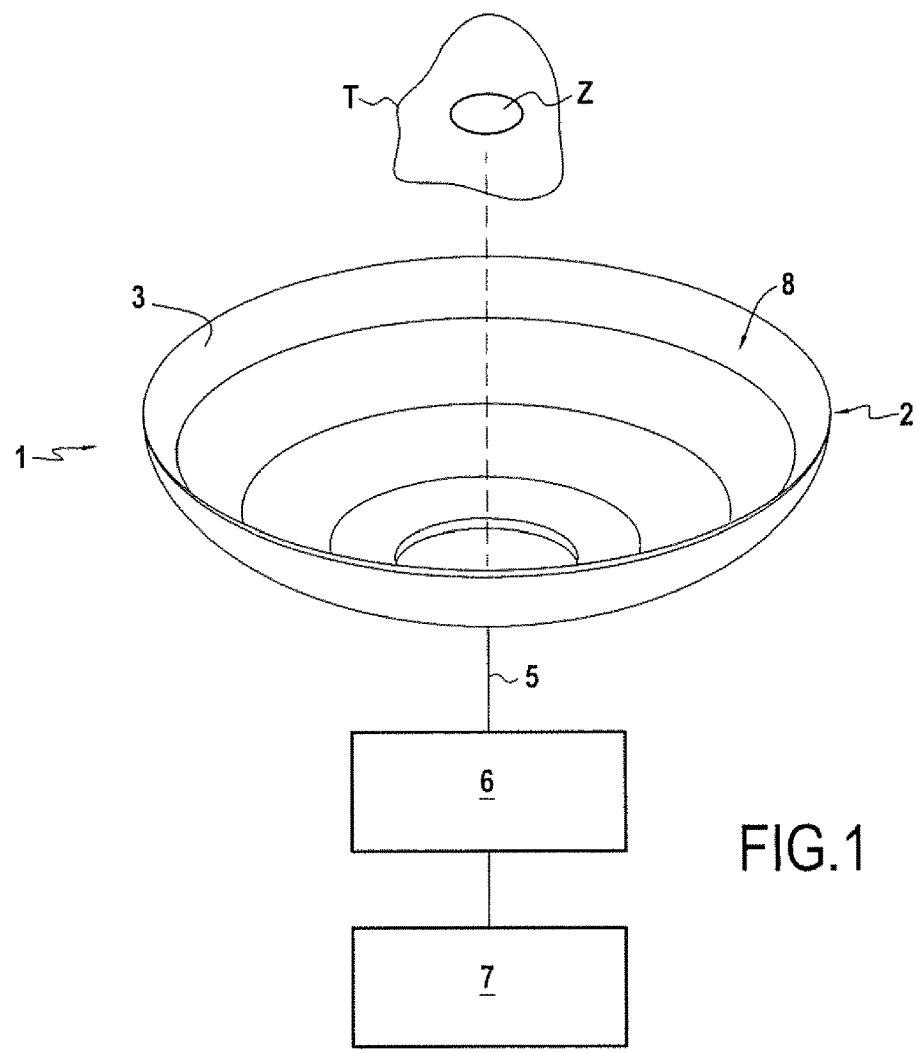
FIG. 1 shows an ultrasound therapy probe having an emission surface of toroidal shape.

In the present description, the invention is described in its application to characterizing an ultrasound lesion in organic tissues caused by applying high intensity focused ultrasound. The ultrasound is delivered by a therapy probe 1 shown in FIG. 1 having an emission surface that is toroidal in shape. The therapy probe 1 is adapted to treat tissue in a living being by means of high intensity focused ultrasound (HIFU). The therapy probe 1 includes in particular a transducer 2 having one or more ultrasound emitters 3 such as piezoelectric elements, for example. These ultrasound emitters 3 are connected by coaxial cables 5 via an amplifier stage 6 to a control circuit 7 that delivers signals for activating the ultrasound emitters 3. The control circuit 7 is not described in greater detail since it forms part of the technical knowledge of the person skilled in the art. The control circuit 7 thus comprises in conventional manner a controlled signal generator that is connected to the ultrasound emitters via the amplifier stage 6.

The transducer 2 presents a face 8 for emitting ultrasound waves that are focused on a focal zone Z. As shown more particularly in FIG. 2, this emission face 8 is a surface of revolution generated by rotating around an axis of symmetry S a concave or convex curve segment 9 of length l presenting a center of curvature C and located at a distance R from the axis of symmetry S, where R is not zero. The surface of revolution 8 is generated by a circularly arcuate segment of length l, of radius r, and of center c that lies at a distance R from the axis of symmetry S, where R is not zero. The shape of this surface of revolution 8 is considered to be a toroidal shape.

Figure 2:
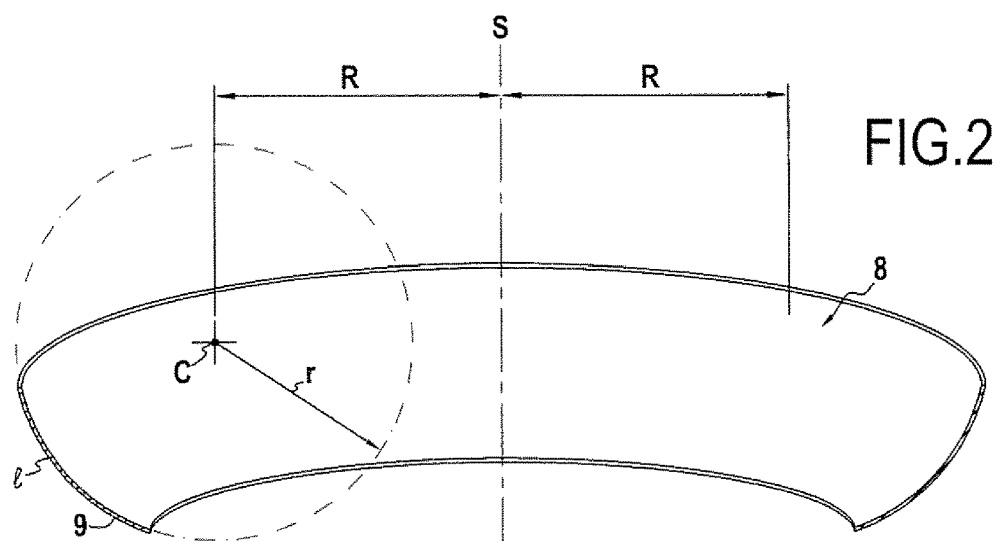
FIG. 2 is a diagram showing the use of such a probe for treating organic tissues.

In the example shown in FIG. 2, the center of curvature C and the curve segment 9 are located on the same side of the axis of symmetry S. It should be observed that provision could be made for the center of curvature C to be situated on the side of the axis of symmetry S that is opposite from the curved segment 9. In this variant, the emission face 8 is considered to be the result of a crossed toroidal shape.

In the embodiment shown in FIG. 2, the surface of revolution 8 is generated by a circularly arcuate segment having its concave side facing towards the axis of symmetry S. Naturally, the surface of revolution 8 may be generated by a segment of a curve other than a circular arc. Thus, the surface of revolution 8 may be generated by a segment of a curve for which the distance r between each point of the curve segment and the center of curvature C presents variation that is continuous (without any point of inflection), e.g. such as an elliptical curve segment.

As can be seen from the above description, the emission face 8 of the transducer is of toroidal shape. In general manner, the emission face 8 of the transducer presents a shape that is a function of the shape of the curve segment generating the ultrasound emitting surface by being rotated about an axis of symmetry, which curve segment may present a variety of shapes. Thus, by way of example, the emission face 8 may be generated by moving two symmetrical curve segments in translation in a direction perpendicular to the profile plane containing the two curve segments. Each curve segment is concave in shape and of finite length. In this variant, the emission face 8 presents a pseudo-cylindrical shape.

Figure 3:
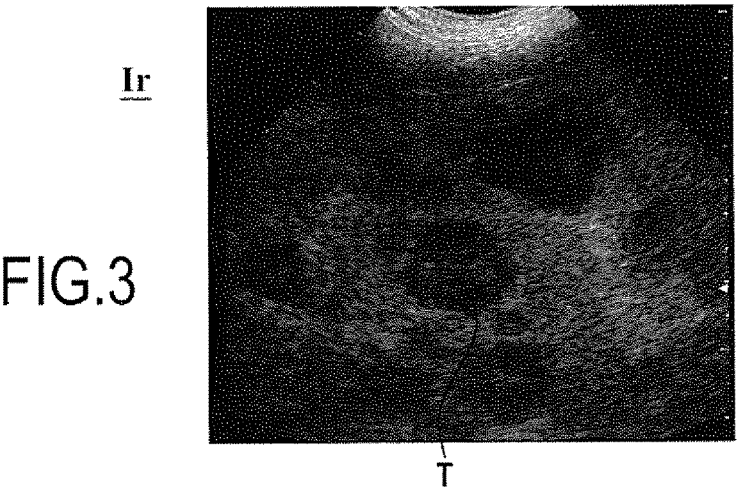
FIG. 3 is an echographic image of a tumor prior to HIFU treatment.

In known manner, the ultrasound probe 1 is positioned by an extracorporeal, peroperative, or endocavity approach so that the focal zone Z of the ultrasound waves has the effect of creating an ultrasound lesion in the organic tissues in the target or treatment zone T corresponding to the tumor that is to be treated. FIG. 3 shows an example of an image Ir of a target zone T corresponding to the tumor to be treated. This "reference" image Ir is a preoperative or peroperative image of the target zone T taken before the HIFU treatment.

Conventionally, the focal zone Z of the ultrasound waves is moved so as to treat all of the target zone T in order to obtain an ultrasound lesion in the target zone T, i.e. tissue necrosis in this zone. Such movement is obtained by moving the ultrasound probe 1 or by electronically controlling the ultrasound emitters 3. This stage of applying ultrasound waves by means of a probe 1 is not described in greater detail since it is well known to the person skilled in the art and does not form part of the subject matter of the invention.

The method of the invention thus seeks to characterize such an ultrasound lesion in organic tissues in the target zone T as obtained by applying high intensity focused ultrasound as delivered by the probe having an emission surface that presents a shape that is toroidal or pseudo-cylindrical. The invention is described in the description below in its application to the example of the liver. Nevertheless, it may also be applied to the tissues of other organs of the human body, such as, for example: the pancreas, the breasts, the uterus, the kidneys, or the placenta.

Figure 4:
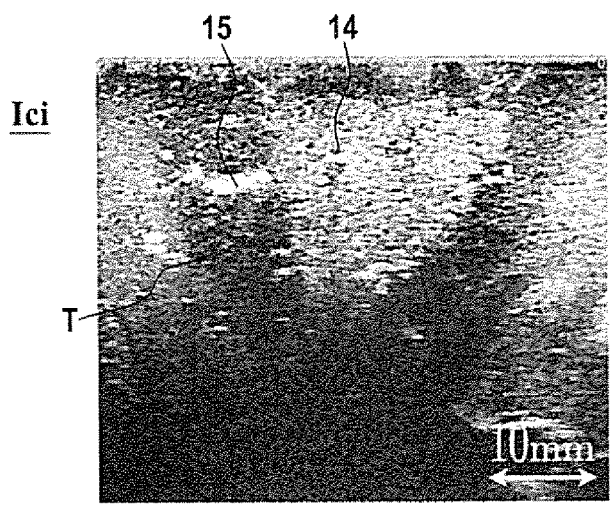
FIG. 4 is an echographic image of a lesion as acquired at the end of applying ultrasound.

FIG. 4 shows an "initial" characterization image Ici of the ultrasound lesion as acquired immediately after applying the ultrasound. In the described implementation, FIG. 4 is an echographic image of the target zone T acquired using an ultrasound imaging system. Nevertheless, it should naturally be understood that the invention is not limited to echographic images, but also covers images obtained by MRI or by scanner.

FIG. 4 shows a zone 14 generating high levels of echo that is characteristic of the ultrasound lesion. During the heating as a result of focused ultrasound, the hepatocytes or cells of the liver in the focal zone are destroyed. In this necrosed zone, numerous cavities appear. Each cavity is located at the center of a liver lobule and coincides with the central vein. The presence of these cavities or tissue gaps explains the high level echo appearance of this ultrasound lesion zone 14.

Furthermore, the characterization image Ici also shows a low-level echo zone 15 located close to the high-level echo zone 14, which zone 15 was subjected during the application of ultrasound waves to a rise in temperature to a temperature lower than the temperature in the high-level echo zone 14. In this low-level echo zone 15, the ultrasound treatment gives rise to cell lysis, with destruction of the cytoplasmic organelles that were initially present in the hepatocytes. The disappearance of these organelles explains the low-level echo appearance of this lesion zone 15 surrounding the necrosed zone 14.

Figure 5:
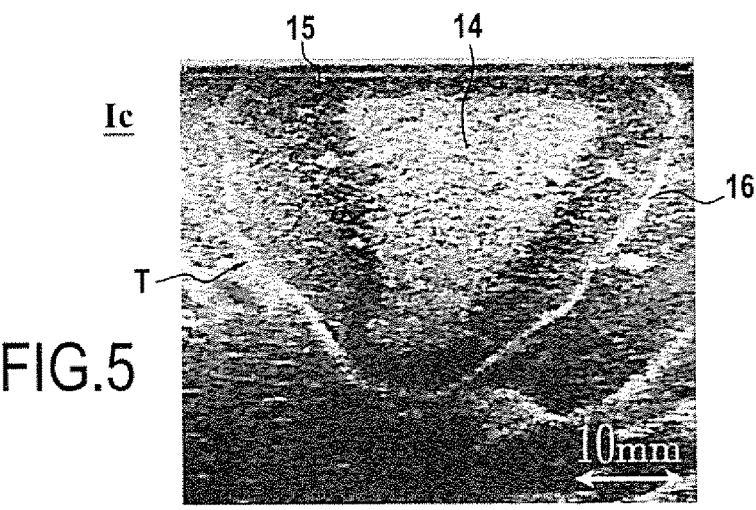
FIG. 5 is an echographic image of a lesion as acquired after a period of eight days measured from the end of applying ultrasound.

The invention thus sets out to characterize the ultrasound lesion T corresponding to the high-level echo zone 14 and to the low-level echo zone 15. For this purpose, the method of the invention consists initially, after a period of at least two days from the end of applying ultrasound, in acquiring at least one characterization image Ic for characterizing the organic tissues. The period of at least two days preferably lies in the range six days to thirty days and typically is about eight days. This characterization image Ic, shown in FIG. 5, is an echographic image of the treated zone taken by an ultrasound imaging system, however it is clear that such a characterization image could be obtained by imaging systems of some other type.

According to an essential characteristic, the method then consists in detecting the presence of a contrast border 16 in the characterization image Ic in order to determine the extent of the lesion. The term "contrast border" should be understood to mean a more or less continuous line of narrow width that presents light intensity that is greater than that of the surrounding tissues corresponding to a high-level echo signal. The contrast border 16 appears pale in the example shown in FIG. 5. Advantageously, the method consists in detecting in this image the presence of a contrast border 16 that presents a closed outline.

Advantageously, it is found that this border can easily be detected in an image obtained by conventional ultrasound imaging, i.e. of the B-mode type (two-dimensional brightness mode), of the kind that is presently widely available at low cost and without needing to have recourse to complex image processing algorithms seeking to enhance contrasts that are insufficient between zones that have been treated and zones that have not been treated. The method makes it possible to detect a contrast border by detecting a discontinuity in the acoustic impedance of the analyzed tissues, which acoustic impedance discontinuity is detected directly and visible in conventional B-mode ultrasound imaging without requiring any particular additional processing.

It should be understood that during HIFU treatment, the heat delivered by ultrasound emission weakens the plasma membranes of peripheral cells. Such damaged membranes then become porous. By the osmosis effect, a large quantity of calcium penetrates into the cytoplasm. If the cell is still functional, regulation of the intracellular concentration of calcium is then performed by mitochondria. When the ion concentration increases, the mitochondria convert the dissolved calcium into a solid precipitate. Since this phenomenon is permanent, each mitochondrion then becomes a crystal seed enabling crystal growth to be initialized. Thereafter, a multitude of calcium grains as formed in this way cause the border 16 to be formed.

Typically, in the echographic image, the border 16 generates high-level echoes. More precisely, the border 16 is formed by precipitates of hydroxyapatite. In the characterization image, and as explained above, numerous islands of solid material appear corresponding to agglomerations of precipitated calcium. Between applying the ultrasound and taking the characterization image, the organism has created a shell of calcium around the lesion properly speaking. The discontinuity in acoustic impedance caused when ultrasound passes from liver tissue to the calcified medium leads to a high-level echo signal being created in the characterization image Ic, which signal takes the form of the contrast border.

The appearance of this border 16 over time, after a period of at least two days and typically of at least six days, makes it possible to monitor which zones were destroyed as a result of the ultrasound treatment. The hepatocytes situated outside the border 16 are not destroyed irreversibly and present normal functioning without precipitating calcium. Conversely, the hepatocytes situated within the border 16 have been subjected to heating due to the HIFU treatment and are characterized by irreversible coagulation necrosis. Since their functioning has been destroyed completely, those hepatocyes do not precipitate any calcium. The hepatocytes situated in the transition zone between healthy tissue and destroyed tissue are merely weakened, and they conserve sufficient activity to precipitate calcium and form the contrast border. The border 16 thus serves to characterize the extent of the ultrasound lesion T.

The formation of the high-level echo and low-level echo zones 14 and 15 and the formation of the border 16 are the result of the toroidal or pseudo-cylindrical shape of the ultrasound transducer 2 that was used. In comparison with present technologies (spherical shape) for focusing ultrasound waves in small volumes that are juxtaposed with one another, toroidal or pseudo-cylindrical shapes enable ultrasound energy to be deposited massively in a large volume creating a vast central zone that has been subjected to intense insonification and in which cavities form giving the high-level echo appearance. At the periphery of this zone, insonification is less intense and leads merely to cell lysis, which appears in the form of a low-level echo image. The contrast border 16 is formed by cells situated at the end of the transition zone between the lysed cells and healthy cells.

As can be seen more clearly in FIG. 5, the border 16 surrounds the low-level echo zone 15, which itself surrounds the high-level echo zone 14, as explained above. The low-level echo and high-level echo zones 15 and 14 remain present in the characterization image Ic. Once the border 16 has been detected in the characterization image Ic, the invention advantageously makes it possible to identify the ultrasound lesion T, i.e. the high-level echo zone 14, and the low-level echo zone 15 that is located close both to the high-level echo zone 14 and to the contrast border 16.

Thus, in the invention, it suffices to identify the presence of the border 16 in the characterization image Ic in order to determine the extent of the lesion. This identification of the border 16 in order to determine the extent of the ultrasound lesion in accordance with the invention can be performed visually or by using digital image processing. Typically, detecting the border 16 consists in using image processing to detect a closed border or a closed loop made up of a set of points.

In a preferred implementation of the invention, the method consists in acquiring a reference image Ir of organic tissues before applying ultrasound, in order to visualize the tumor, e.g. such as the image shown in FIG. 3. The method consists in comparing the reference image Ir with the characterization image Ic in order to verify the size of the margin and confirm that negative margins are present.

Furthermore, comparing the reference and characterization images Ir and Ic makes it possible to deduce a margin size for the extent of the lesion. In the invention, this can be done merely by calculating a ratio between the area defined by the ultrasound lesion in the characterization image Ic and the area defined by the tumor in the reference image Ir in order to deduce a margin size for the extent of the ultrasound lesion. In an advantageous implementation, the invention consists in taking a plurality of reference images Ir and a plurality of characterization images Ic. This makes it possible to determine firstly a volume defined by the ultrasound lesion in the characterization images Ic and secondly the volume defined by the tumor in the reference images Ir, and then to deduce therefrom a margin size for the extent of the ultrasound lesion as a function of the volumes.

The invention is not limited to the examples described and shown since various modifications may be applied thereto without going beyond its ambit.

The invention claimed is:

1. A method of determining an extent of an ultrasound-generated lesion in an organic tissue, the ultrasound generated lesion being made by applying high intensity focused ultrasound delivered by a probe comprising an emission surface having a shape that is toroidal or pseudo-cylindrical, the method comprising:
acquiring a reference image of the organic tissue prior to applying the high intensity focused ultrasound;
applying the high intensity focused ultrasound delivered by the probe;
after a period of at least two days, but less than thirty days, from the end of the high intensity focused ultrasound application, acquiring at least one characterization image of the organic tissue;
detecting a presence of a contrast border in the characterization image using digital image processing;
wherein the contrast border is in a form of a line having a light intensity that is greater than a light intensity of surrounding tissue;
wherein the contrast border corresponds to precipitated calcium; and
determining the extent of the ultrasound-generated lesion from the contrast border after processing the reference and characterization images using digital image processing.

2. The method according to claim 1, wherein the contrast border is a closed contrast border.

3. The method according to claim 1, comprising acquiring the characterization image after a period in a range of from six days to thirty days.

4. The method according to claim 1, wherein the organic tissue is liver tissue.

5. The method according to claim 1, comprising acquiring the characterization image after a period of eight days.

6. The method according to claim 1, wherein precipitated calcium comprises agglomerations of precipitated calcium.

7. The method according to claim 1, comprising identifying, within the contrast border, a high-level echo zone and a low-level echo zone located between the high-level echo zone and the contrast border.

8. The method according to claim 7, comprising calculating a ratio between the area defined by the ultrasound-generated lesion in the characterization image and the area defined by a tumor in the reference image.

9. The method according to claim 1,
comprising comparing the reference image with the characterization image in order to monitor therapeutic margins.

10. The method according to claim 9, comprising:
acquiring a plurality of reference images of the organic tissue prior to applying the high intensity focused ultrasound;
after a period of at least two days, but less than thirty days, from the end of the high intensity focused ultrasound application, acquiring a plurality of characterization images of the organic tissue; and
using the plurality of characterization images and the plurality of reference images to calculate a ratio between a volume defined by the ultrasound-generated tissue lesion in the plurality of characterization images and the volume defined by a tumor in the reference images.

11. A method of treating and characterizing a biological tissue in a mammal, the method comprising:
acquiring a reference image of the biological tissue prior to applying high intensity focused ultrasound to the biological tissue;
applying high intensity focused ultrasound to the biological tissue using a probe comprising an emission surface having a shape that is toroidal or pseudo-cylindrical;
after a period of at least two days, but less than thirty days, from the end of the high intensity focused ultrasound application, acquiring at least one characterization image of the biological tissue;

detecting a presence of a contrast border in the characterization image using digital image processing;

wherein the contrast border is in a form of a line having a light intensity that is greater than a light intensity of surrounding tissue;

wherein the contrast border corresponds to precipitated calcium; and determining, from the contrast border, an extent of a lesion in the biological tissue made by applying the high intensity focused ultrasound, after processing the reference and characterization images using digital image processing.

12. The method according to claim 11, wherein the mammal is a human.

13. The method according to claim 11, wherein the contrast border that is detected is a closed contrast border.

14. The method according to claim 11, comprising identifying, within the contrast border, a high-level echo zone and a low-level echo zone located between the high-level echo zone and the contrast border.

15. The method according to claim 11, comprising comparing the reference image with the characterization image in order to monitor therapeutic margins.

16. The method according to claim 11, comprising calculating a ratio between the area defined by the ultrasound-generated lesion in the characterization image and the area defined by a tumor in the reference image.

17. The method according to claim 11, comprising:

acquiring a plurality of reference images of the biological tissue prior to applying the high intensity focused ultrasound;

after a period of at least two days, but less than thirty days, from the end of the high intensity focused ultrasound application, acquiring a plurality of characterization images of the biological tissue; and using the plurality of characterization images and the plurality of reference images to calculate a ratio between a volume defined by the ultrasound-generated lesion in the plurality of characterization images, and the volume defined by a tumor in the reference images.

18. The method according to claim 11, comprising acquiring the characterization image after a period of from six days to thirty days.

19. The method according to claim 11, comprising acquiring the characterization image after a period of eight days.

20. The method according to claim 11, wherein the biological tissue is liver tissue.

21. The method according to claim 11, wherein the mammal is a human.

22. The method according to claim 11, wherein precipitated calcium comprises agglomerations of precipitated calcium.

* * * * *